United States Patent [19]
Morris

[11] Patent Number: 5,483,955
[45] Date of Patent: Jan. 16, 1996

[54] OXYGEN RESERVOIR BAG FOR A SQUEEZE BAG RESUSCITATOR

[75] Inventor: Gregory R. Morris, North Huntingdon, Pa.

[73] Assignee: Respironics, Inc., Murrysville, Pa.

[21] Appl. No.: 312,702

[22] Filed: Sep. 27, 1994

[51] Int. Cl.⁶ ............................... A02B 7/04; B65D 81/20
[52] U.S. Cl. ................... 128/205.13; 128/204.28; 383/44
[58] Field of Search .................... 383/3, 44; 128/202.28, 128/203.11, 203.12, 203.28, 203.29, 204.18, 204.28, 205.13, 205.14, 205.15

[56] References Cited

U.S. PATENT DOCUMENTS

| | | | |
|---|---|---|---|
| 2,677,371 | 5/1954 | Serra | 128/205.17 |
| 3,090,380 | 5/1963 | Dold | 128/205.13 |
| 3,650,268 | 3/1972 | Ruben. | |
| 4,239,038 | 12/1980 | Holmes. | |
| 4,532,923 | 8/1985 | Flynn. | |
| 4,537,191 | 8/1985 | Blumensaadt. | |
| 4,774,941 | 10/1988 | Cook. | |
| 5,279,289 | 1/1994 | Kirk | 128/205.23 |
| 5,427,091 | 6/1995 | Phillips | 128/205.15 |

FOREIGN PATENT DOCUMENTS

| | | | |
|---|---|---|---|
| 0192348 | 8/1986 | European Pat. Off. | 383/44 |
| 689788 | 9/1930 | France | 128/203.28 |
| 28402 | 1/1898 | United Kingdom | 128/203.28 |

*Primary Examiner*—Ren Yan
*Assistant Examiner*—Eric P. Raciti
*Attorney, Agent, or Firm*—Reed Smith Shaw & McClay

[57] ABSTRACT

A resuscitator apparatus including a resilient, self-inflating squeeze bag having a single combined inlet/outlet which is preferably removably connected to a first manifold in operative communication with a valve device. The first manifold includes an inlet coupling adapted for connection to a source of pressurized respiratory gas such as oxygen and an outlet coupling adapted for connection to a first end of a tubular connector. The second end of the tubular connector is adapted for connection to an inlet coupling of a second manifold in operative communication with a non-rebreathing valve contained within a tubular, preferably L-shaped housing. The tubular housing includes a first leg connected to the second manifold and a second leg extending substantially perpendicular to the first leg, the second leg being adapted for connection to a subject interface member such as a breathing mask. An oxygen reservoir bag preferably formed of thin, pliable plastic surrounds the tubular connector and is sealingly attached without supplemental fasteners to the first and second manifolds. The oxygen reservoir bag is provided with at least one radially outwardly projecting pocket having an aperture. Upon inflation of the oxygen reservoir bag, the at least one pocket inflates to form a bulbous formation which bulges from the bag while the aperture vents excess oxygen to the atmosphere.

15 Claims, 11 Drawing Sheets

OXYGEN RESERVOIR BAG FOR A SQUEEZE BAG RESUSCITATOR

FIELD OF THE INVENTION

The present invention relates in general to breathing assistance apparatus and, more particularly, to an oxygen reservoir bag for resuscitator apparatus of the "squeeze bag" type.

BACKGROUND OF THE INVENTION

Resuscitation, as that term is herein used, refers generally to externally exerted efforts to assist or restore breathing of a patient whose natural breathing has either become impaired or has ceased, or to at least temporarily attempt to emulate the effects of more natural breathing in the patient. Resuscitation involves forcing air or oxygen under appropriate pressure through the patient's natural airway system and into his lungs to inflate the latter at appropriate intervals separated by periods during which such application of air or oxygen under pressure is interrupted (and an external physical pressure may be applied to the patient's chest) to permit the previously applied air to escape from the patient's lungs and the latter to deflate.

The forms of previous resuscitators of greatest interest as background for this invention, commonly called "squeeze bag" or "bag-valve-mask" resuscitators, employ some type of manually compressible and self-restoring bag having the interior thereof in fluid communication with a face mask. In its most primitive conceptual form, such a device could be operated for resuscitation purposes simply by applying the mask to the face of a patient, manually squeezing the bag to force air from the bag through the mask and into the patient's lungs, releasing the squeezing pressure from the bag and removing the mask from the patient's face to permit escape of air from the patient's lungs. At the same time, the bag would restore itself and thereby self-inflate with fresh atmospheric air through the mask. The bag would then remain in its restored condition until the next bag squeezing operation and such cycle would be repeated as necessary. A squeeze bag resuscitator thus permits a trained person administering treatment to directly control both the quantity of air forced into the patients lungs and the intervals of doing so to best suit the condition of the patient through choice of the extent and timing of squeezing of the bag.

Even relatively early squeeze bag resuscitators soon incorporated various refinements, including employment of resilient squeeze bags adapted to be conveniently held in one hand with the face masks carried more or less directly on the frontal extremities of the bags to increase portability and facilitate use by a single person. A bag fill valve (an inward flow permitting check valve for communicating the interior of the bag with the atmosphere) was introduced to permit refilling of the bag with fresh air during its restoration phase without removing the mask from the face of the patient, And, in conjunction with the bag fill valve came the evolution of the patient non-rebreathing valve assembly. Such assembly is interposed between the bag and the mask and permits fresh air to move from the bag into the mask during the squeeze phase, but vents to the atmosphere air returned to the mask from the patient's lungs during the bag restoration or restored phases, thereby preventing passage of the expired air into the bag from which it would be forced back into the patients lungs or "rebreathed" during the next squeeze phase.

During the course of development of squeeze bag type resuscitators, it was recognized that it would be desirable to administer oxygen, or at least oxygen enriched air, rather than merely atmospheric air, in treating some resuscitation patients.

Accordingly, the development of practical means for introducing oxygen into the squeeze bag initially entailed providing "oxygen enrichment" for the air drawn into the squeeze bag from the atmosphere during the restoration phase of the bag cycle. A common and still prevalent approach to oxygen enrichment is to provide an elongate tube of relatively large diameter having one end thereof in fluid communication with the fill valve opening of the bag (typically at the extremity of the bag opposite from the non-rebreathing valve and mask) and the other end thereof exposed to the atmosphere, together with a considerably smaller tube extending into the larger tube and coupled with a pressurized oxygen source for continuously releasing oxygen into the air entering and accumulating within the large tube from the atmosphere. Such devices are commonly call "oxygen accumulators" and are effective to introduce a mixture of air reasonably enriched with oxygen into the bag during the restoration phase of its cycle, without significantly increasing the pressure within the bag (since one end of the large tube of the accumulator is in free communication with the atmosphere). Examples of these and other oxygen accumulator resuscitators may be found in U.S. Pat. Nos. 4,501,271, 4,774,941, 4,821,713, 5,067,487, 5,109,840, 5,140,982 and 5,279,289. A notable shortcoming of resuscitators of this sort is that the concentration of the continuously flowing oxygen gas is subject to dilution by the ambient air with which it is mixed.

Further, the advent of the oxygen accumulator squeeze bag resuscitator did not satisfy the need for being able to administer substantially pure oxygen to patients under certain relatively frequently occurring high oxygen demand circumstances, such as resuscitation responsive to cardiac distress or like conditions. The invention disclosed in U.S. Pat. No. 3,796,216, however, represented an early attempt to administer essentially pure oxygen to a subject using a squeeze bag resuscitator. 10 The apparatus disclosed therein included a body member, a squeeze bag, an oxygen inlet, a flapper valve and a face mask. The body member comprises a tubular portion to which the mouth of the squeeze bag is connected. The face mask is joined to the tubular member generally opposite the squeeze bag and an inlet adapted to be connected to a source of breathing gas such as oxygen is provided in the tubular member between the squeeze bag and the face mask. The flapper valve resides in the body member and regulates passage of oxygen from the squeeze bag to the face mask.

Unlike those discussed above, the squeeze bag disclosed in U.S. Pat. No. 3,796,216 is not self-restoring but merely flexible or pliable and is continuously inflated with oxygen via the oxygen inlet. When the bag is sufficiently inflated and it is desired to administer oxygen to the subject, the user squeezes the bag to increase the pressure in the tubular member to a level sufficient to cause the flapper valve to expose a mask inhalation port and cover a mask exhalation port whereby the oxygen is passed into the mask for consumption by the subject. Once the contents of the bag have been depleted via squeezing to an extent that the pressure in the body member is insufficient to overcome the bias of the flapper valve, the valve returns to its normal position covering the inhalation port and exposing the exhalation port. At this time, the subject exhales, his expiratory gases passing through the exhalation port, and the bag reinflates. This process is repeated as necessary to facilitate or restore the patients normal breathing pattern.

A functional weakness of this sort of resuscitator is that it is incapable of dispensing pressurized atmospheric air in the event of failure or exhaustion of the pressurized oxygen supply. Specifically, even if the gas source were disconnected from the gas inlet thereby exposing the inlet to the atmosphere, the squeeze bag is not self-restoring. Hence, it cannot create either the negative pressure required to draw air into the inlet or the positive pressure to expel the air therefrom.

U.S. Pat. Nos. 2,399,643, 2,834,339, 3,196,866, 3,316,903, 3,473,529, 4,037,595, 4,077,404, 4,088,131 and 4,121,580 describe self-distending squeeze bag or similar resuscitators variously capable of administering air, oxygen or a mixtures thereof upon compression of the squeeze bag.

The assignee of the present invention, Respironics, Inc. of Murrysville, Pa., has developed a simplified and compact squeeze bag resuscitator, discussed at greater length hereinafter, which permits the subject to consume essentially pure oxygen. The oxygen is delivered to a first manifold that is in fluid communication with an oxygen reservoir bag, a first flapper valve and a second flapper valve. A length of conduit joins the first manifold with a second manifold and delivers the contents of the squeeze bag from the first to the second manifold. The second manifold carries a third flapper valve for relieving excess pressure in the oxygen reservoir bag, which bag surrounds the conduit and is also sealingly connected at its opposite ends to the first and second manifolds. In addition, a non-rebreathing valve and breathing mask are connected to the second manifold in conventional fashion.

In operation, the first flapper valve regulates gas flow into the squeeze bag and the second flapper valve regulates ambient air flow into the manifold. Under normal conditions, the oxygen initially fills the reservoir bag and, if the squeeze bag is in a restoring phase, oxygen flows past the first flapper valve and into the squeeze bag. Alternatively, if the bag is fully restored and the subject inhales, the oxygen may pass the first flapper valve and flow directly to the subject. If, however, the bag is fully restored and the subject is not inhaling, the third flapper valve operates to vent excess oxygen pressure from the oxygen reservoir bag. The third flapper valve prevents excessively high pressure oxygen from reaching the patient's lungs and causing over-inflation and possible physical damage thereto. This valve additionally serves to limit the effect of incoming oxygen pressure on exhalation resistance commonly known as AutoPEEP (automatic positive end expiratory pressure). When internal resuscitator pressure is increased, AutoPEEP manifests itself in increased pressure on the backside or "patient" side of the non-rebreathing valve which, in turn, correspondingly increases the effort exerted by the patient to exhale.

A disadvantage of providing a third flapper valve in the second manifold, however, is that the inclusion of such an element in the resuscitator apparatus unnecessarily complicates construction and adds to the cost of the apparatus.

It has alternatively been proposed to provide one or more apertures or vents in the oxygen reservoir bag such that the bag itself may vent excess oxygen to the atmosphere. An oxygen reservoir bag is typically formed of flexible plastic material and is generally oblate spheroidal in configuration, the "hemispheres" of which spheroid are joined at an equatorial region by heat sealing or other suitable bonding process. In the past, attempts have been made to form the vents simply by cutting one or more notches from the heat seal band produced at the equatorial region by the bonding process. It has been discovered, however, that to cut notches in the bag compromises the venting performance characteristics of the bag. For instance, at low incoming oxygen flow rates, e.g., when incoming oxygen flow is approximately 5 to 10 liters per minute, depending upon vent geometry, delivered oxygen concentration may be less than desirable under normal resuscitator cycling because atmospheric air may enter the bag with minimal resistance whereupon it becomes mixed with the incoming oxygen. Vent geometry also affects AutoPEEP. Thus, a particular vent geometry may be suitable for delivering satisfactory oxygen concentration at low incoming oxygen flow, yet at elevated incoming flow rates, the user may experience excessive AutoPEEP.

As an alternative to notching the reservoir bag's equatorial heat seal band, Respironics, Inc. has developed a thin reservoir bag whose equatorial region is provided with one or more radially projecting flaplike vents. Nevertheless, that design has been found to engender yet another problem, namely, the limp and protruding flap vents tend to randomly fold over and occlude under working pressure, thereby vitiating the intended effect of continuous and reliable venting of excess oxygen. To overcome this problem, it has been suggested to increase the thickness of the walls of bag including the flap vents themselves. This approach, however, produces undesirable consequences. That is, increasing bag thickness proportionately increases material cost. And, a thicker bag results in a more rigid bag that is less responsive to the pressure fluctuations within the resuscitator apparatus. Thus, a thick oxygen reservoir bag is less able to properly contract and expel its charge of oxygen upon restoration of the squeeze bag from a collapsed to a distended condition.

An advantage exists, therefore, for a squeeze bag type resuscitator including a very thin, highly flexible, yet rugged oxygen reservoir bag capable of readily collapsing and delivering essentially pure oxygen upon demand for oxygen stored in the bag, and of continuously and reliably venting excess oxygen between oxygen demand episodes.

The oxygen reservoir bag of the previously discussed Respironics, Inc. resuscitator is also open at its opposite ends or "poles" whereat it is taped or otherwise adhesively and sealingly secured to the first and second manifolds. So constructed, the oxygen reservoir bag establishes a sealed oxygen chamber about the conduit and between the manifolds. A disadvantage of this arrangement is that the additional materials (e.g., tape or adhesive) and attendant labor required to adhesively secure the opposite ends of the oxygen reservoir bag to the manifolds undesirably contribute to the manufacturing cost of the resuscitator. Moreover, if care is not taken in the attachment of the oxygen reservoir bag to the manifolds, oxygen may unintentionally leak from the system at one or both of the manifolds.

U.S. Pat. Nos. 4,917,081 and 4,919,132 teach pliable breathing gas storage bags connected at their opposite ends to components of respiratory apparatus. The bag in U.S. Pat. No. 4,917,081 requires supplemental attachment means to assure its sealing connection. The bag in U.S. Pat. No. 4,919,132 merely receives smooth tubular inserts having no structure to which the bag may positively and sealingly engage to prevent gas leakage from the bag.

In connection with a resuscitator of the type having an oxygen reservoir bag, an advantage exists, therefore, for an improved system by which the oxygen reservoir bag may be sealingly attached to the resuscitator without resort to adhesive tape or other superfluous fastening means.

SUMMARY OF THE INVENTION

In accordance with the present invention, there is provided a novel oxygen reservoir bag for a squeeze bag type resuscitator apparatus and a novel squeeze bag resuscitator apparatus incorporating such bag. The oxygen reservoir bag enhances apparatus performance and durability while simultaneously producing an apparatus that is uncomplicated in design, easy to manufacture and low in cost.

Generally, the resuscitator apparatus comprises a resilient, self-inflating squeeze bag having a single combined inlet/outlet which is preferably removably connected to a first manifold in operative communication with a valve means. The first manifold includes an inlet coupling adapted for connection to a source of pressurized respiratory gas such as oxygen and an outlet coupling adapted for connection to a first end of a flexible tubular connector or conduit. The second end of the tubular connector is adapted for connection to an inlet coupling of a second manifold in operative communication with a conventional patient valve, such as, for example, a non-rebreathing valve contained within a tubular, preferably L-shaped housing. The tubular housing includes a first leg connected to the second manifold and a second leg extending substantially perpendicular to the first leg, the second leg being adapted for connection to a subject interface member such as a breathing mask or the like.

An oxygen reservoir bag of generally oblate spheroidal configuration preferably formed of thin, pliable plastic film surrounds the tubular connector and is sealingly attached at first and second ends or "poles" thereof to the first and second manifolds, respectively. According to a preferred embodiment, the ends of the oxygen reservoir bag are attached to the manifolds without supplemental fastening means such as adhesives.

When it is desired to administer oxygen to a subject, a pressurized oxygen source is connected via suitable means such as flexible hose to the inlet coupling of the first manifold. The inlet coupling is fluidly coupled to an interior passageway provided in the first manifold, which passageway communicates with the interior of the oxygen reservoir bag. Hence, by flowing through the inlet coupling and the interior manifold passageway, the oxygen serves to inflate the oxygen reservoir bag. Simultaneously, the interior passageway delivers the pressurized oxygen to a first flapper valve element which regulates oxygen flow from the interior of the oxygen reservoir bag to the interior of the squeeze bag. A second flapper valve element situated in the first manifold is in regulated communication with the ambient atmosphere and controls ingress of atmospheric air into the interior of the first manifold through ambient air inlet port means also provided in the first manifold. The function of the first and second valve elements will be more fully appreciated from the following discussion.

The oxygen reservoir bag is provided with at least one radially outwardly projecting pocket generally situated at an equatorial region thereof. Each pocket includes vent means, preferably an elongated vent slot extending in a direction substantially normal to and spanning the equator of the bag. The pockets form bulbous formations that resist occlusion when the oxygen reservoir bag is internally pressurized and continuously vent excess oxygen at steady and predictable flow rates, as well as enhance delivered oxygen concentration when incoming oxygen flow rates are low. So constructed and arranged, the pockets and their attendant vent slots enable the reservoir bag to be manufactured to minimal thicknesses. Consequently, a very thin, highly flexible, rugged and inexpensive oxygen reservoir bag is realized which is capable of readily collapsing and delivering essentially pure oxygen upon demand for oxygen stored in the bag, and of continuously and reliably venting excess oxygen between oxygen demand episodes.

To operate the resuscitator apparatus, the breathing mask may be placed in sealing engagement with the subject's face covering his mouth and nose, whereby resuscitation may begin. Oxygen is then supplied by initiating flow from a pressurized oxygen source to effect inflation of the oxygen reservoir bag (with any excess oxygen being vented through the respective vent slots formed in the bulbous formations). The operator then squeezes the squeeze bag which urges the first valve element to cover and seal the interior manifold passageway. This action simultaneously ceases oxygen flow into the squeeze bag and expels the gaseous contents thereof sequentially through the first manifold, the tubular connector, the second manifold, the non-rebreathing valve, the tubular housing and the breathing mask whereby it may be consumed by the subject. Thereafter, the operator relaxes the squeezing force applied the squeeze bag thus permitting it to restore itself to its normal shape. This self-distension of the squeeze bag creates negative pressure within the squeeze bag which causes the first valve member to open whereby oxygen within the oxygen reservoir bag is drawn through the interior manifold passageway and into the squeeze bag. During this time, the subject may exhale whereupon his expiratory gases pass through the non-rebreathing valve to the atmosphere in the manner known in the art.

The volume of the oxygen reservoir bag is desirably greater than the difference in volume of the squeeze bag between its compressed and restored states. Further, the second flapper valve element prevents atmospheric air from entering the resuscitator during an oxygen administration procedure through the ambient air inlet port means, whereby the subject receives the full therapeutic benefits of pure oxygen resuscitation.

Continuing, with the squeeze bag restored (during which time the oxygen reservoir bag begins to reinflate with oxygen), the operator may then squeeze the squeeze bag, thereby closing the first valve element and delivering the oxygen to the subject in the manner described above. The subject may exhale while the user permits the squeeze bag to reinflate and the process may be repeated as circumstances dictate.

In the event the oxygen supply should falter, the second valve element would permit the subject immediate and unrestricted access to atmospheric air. Specifically, upon inhalation, the negative pressure exerted on the second valve element causes that valve element to lift from seating engagement with the ambient air inlet port means. Atmospheric air may then enter the ambient air inlet port means, flow past the second valve element, through the manifold passageway, past the first valve element, and, thereafter, through the tubular conduit, second manifold, non-rebreathing valve, tubular housing and breathing mask.

Lastly, the invention additionally contemplates that the oxygen reservoir bag be self-sealing, i.e., that it sealingly attaches to the first and second manifolds without need of adhesive tape or other fastening means.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments therefor shown, by way of example only, in the accompanying drawings, wherein.

DETAILED DESCRIPTION OF THE INVENTION

Figure 1:
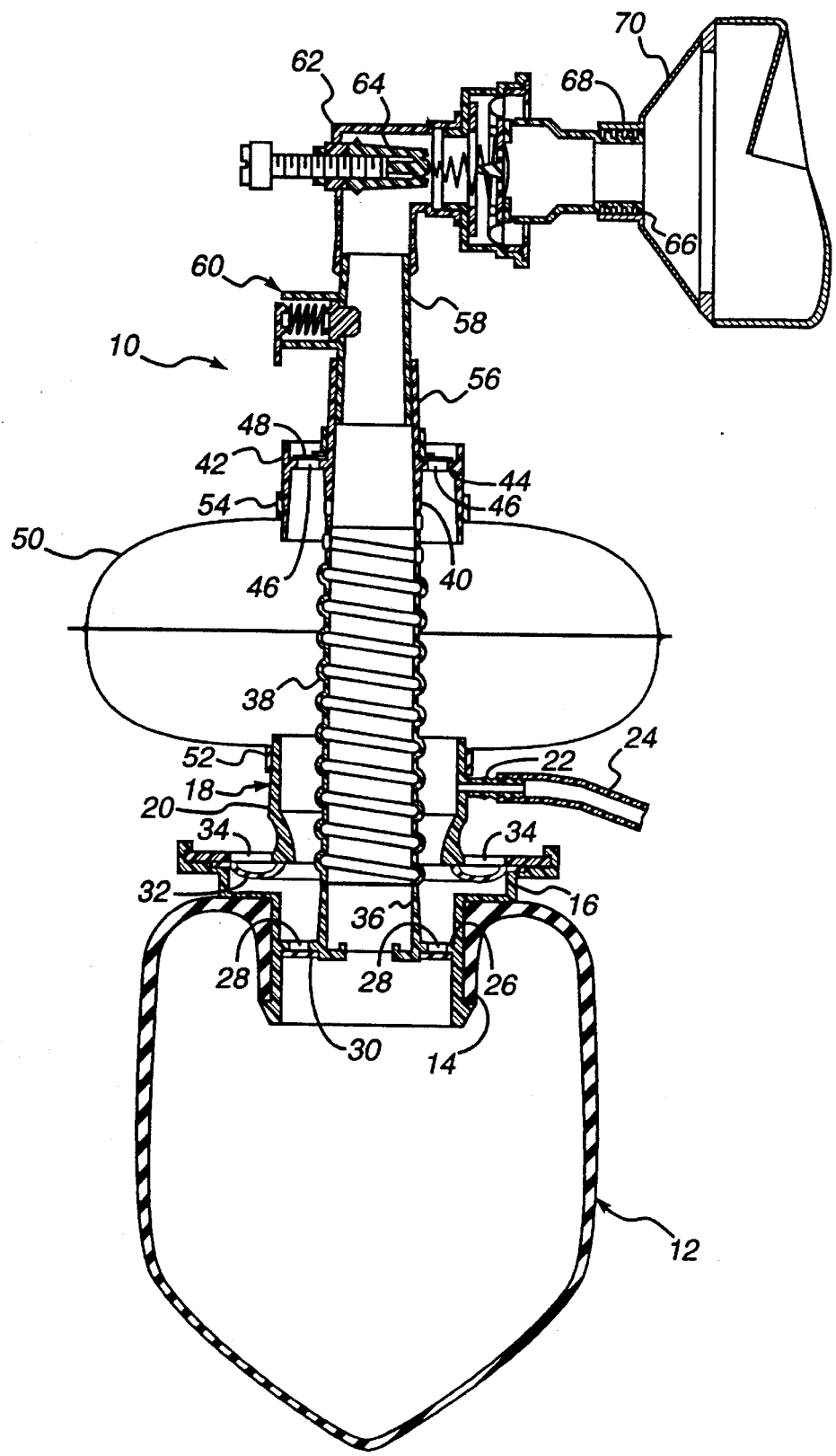
FIG. 1 is an elevational cross-section view of a presently known squeeze bag resuscitator apparatus with its oxygen reservoir bag shown in inflated condition.

In FIG. 1, reference numeral 10 generally represents a fully disposable squeeze bag resuscitator apparatus which is manufactured by Respironics, Inc. of Murrysville, Pa. under the trade name BagEasy®. Apparatus 10 includes a squeeze bag 12 of resilient, self-restoring material such as rubber, neoprene, flexible PVC or the like, having a single annular inlet/outlet opening 14 that is sealingly affixed to a lower housing portion 16 of a first manifold 18 by a suitable adhesive such as cyanoacrylate. An upper housing portion 20 of the first manifold is provided with an oxygen inlet coupling 22 to which a gas delivery means such as flexible conduit 24 may be attached so as to deliver pressurized oxygen from a suitable oxygen source (not illustrated) to the interior of the first manifold.

Integral with and projecting radially inwardly of the first manifold housing is an annular wall 26 provided with a plurality of ports 28 through which atmospheric air and/or pressurized oxygen may be introduced into the interior of squeeze bag 12 in a manner to be described in greater detail later herein in connection with the discussion of FIGS. 3 through 6. An annular, resilient, flapper valve 30 fabricated from flexible synthetic resin or rubber is normally biased into a closed position covering the ports 28 and regulates the flow of gas into the squeeze bag. Reference numeral 32 identifies an annular, resilient flapper valve clamped at its outer periphery between the upper and lower housing portions of the first manifold. Flapper valve 32, like valve 30, is also manufactured from flexible material but, rather than having a simple, flat disc-like cross-sectional shape, is instead formed into an arched, substantially semi-toroidal configuration. Valve 32 assumes this configuration specifically to increase its spring bias and, therefore, its resistance to atmospheric air being introduced into the first manifold through ambient air inlet ports 34 provided in the upper manifold housing portion 20 during resuscitation involving oxygen administration.

A tubular outlet coupling 36 is formed integrally with the annular wall 26 and projects therefrom in a direction opposite that of the squeeze bag. Snugly receiving and preferably adhesively affixed to the outer circumference of the outlet coupling 36 is one end of a flexible corrugated hose 38 the opposite end of which is desirably similarly joined to a tubular inlet coupling 40 of a second manifold 42. Coupling 40 is integral with a radially projecting annular wall 44 of second manifold 42. Annular wall 44 includes a plurality of ports 46 which are normally closed by a thin, flexible, annular flapper valve 48 constructed substantially similar to but having a somewhat lower spring bias than flapper valve 30. A generally oblate, open-ended, oxygen reservoir bag 50 fabricated from thin, non-porous, pliable plastic is sealingly affixed at its opposite ends or "poles" by adhesive tape 52 and 54 to the exteriors, respectively, of the first manifold upper housing portion 20 and the second manifold 42. As a consequence of their respective biases, therefore, when the oxygen reservoir bag 50 is fully inflated (as depicted in FIG. 1), and as oxygen continues to flow into the bag through flexible conduit 24 and first manifold inlet coupling 22, flapper valve 48 yields more easily than flapper valve 30 whereby oxygen overflow is vented through ports 46 to the atmosphere rather than through ports 28 to the interior of the squeeze bag.

Projecting from the side of the annular wall 44 opposite the inlet coupling 40 is a tubular outlet coupling 56 that matingly receives one end of a tubular member 58 that may or may not be fitted with a "pop-off" or similar valve device 60 operable to relieve excess system pressure. The other end of tubular member 58 is joined to the first leg of a generally L-shaped tubular non-rebreathing valve housing 62 which preferably contains therewithin a non-rebreathing valve assembly, generally indicated at 64, of any conventional structure and function known to those in the art. The second leg of housing 62 extends substantially perpendicularly to the first leg thereof and is fitted with an outlet 66 adapted to be frictionally and rotationally received within an inlet 68 of a conventional respiratory mask 70.

Figure 2:
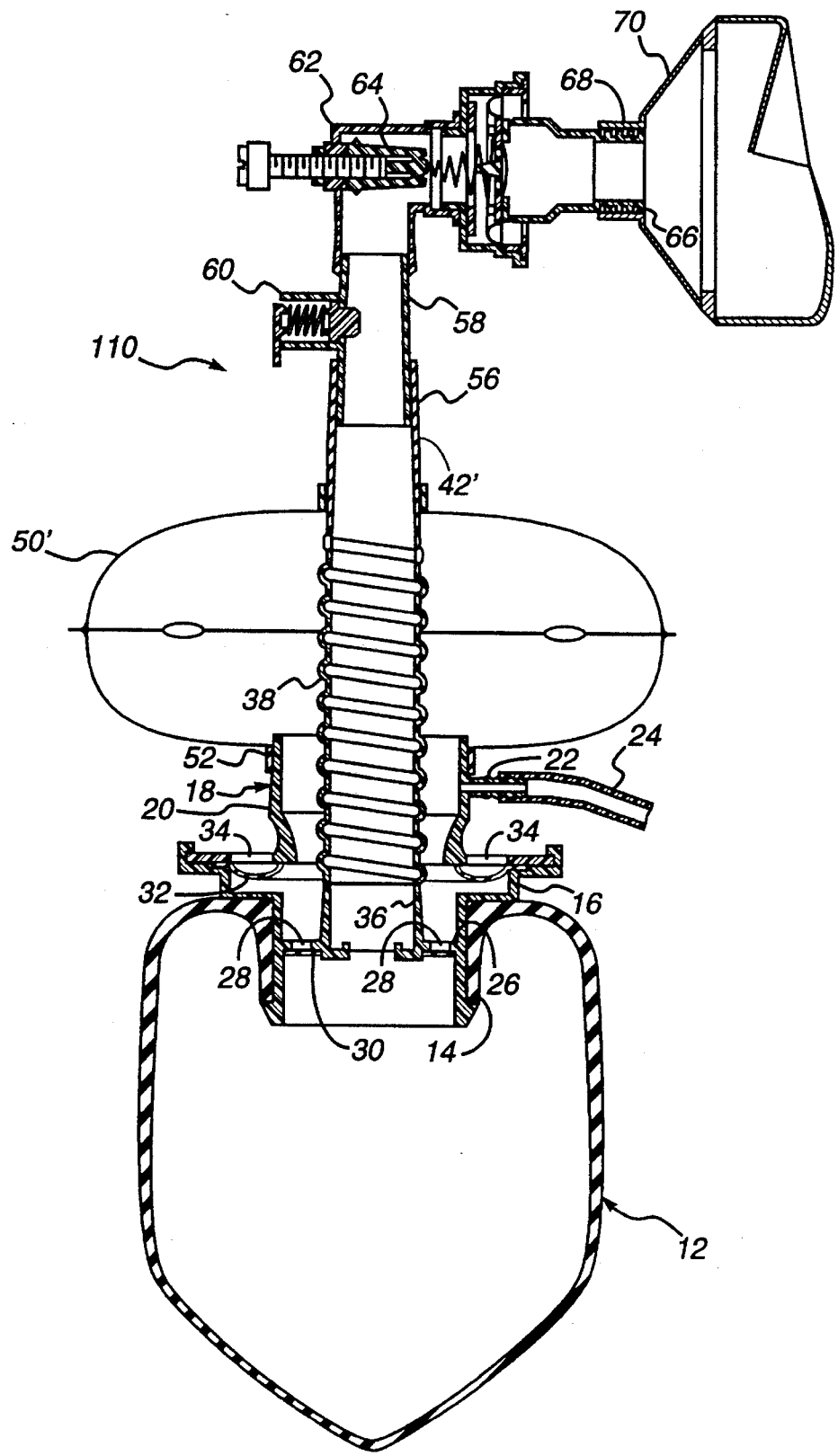
FIG. 2 is an elevational cross-section view of another presently known squeeze bag resuscitator apparatus with its oxygen reservoir bag shown in inflated condition.

Referring to FIG. 2, there is shown another known squeeze bag resuscitation apparatus identified generally by reference numeral 110. Apparatus 110 is constructed and functions generally similarly to apparatus 10 except for differences in the second manifold and oxygen reservoir bag. Indeed, elements of apparatus 110 bearing the same reference numerals as their counterparts in FIG. 1 may be considered substantially identical in structure and function to those FIG. 1 elements unless otherwise indicated. Further, to underscore the differences between the FIG. 1 and FIG. 2 apparatus, the reference numerals representing the second manifold and the oxygen reservoir bag in FIG. 2 bear prime symbols. Hence, the second manifold in FIG. 2 is designated by reference numeral 42' and the oxygen reservoir bag of that figure by reference numeral 50'

Second manifold 42' of apparatus 110 is considerably simpler in design than second manifold 42 of apparatus 10. Specifically, annular wall 44, ports 46 and annular flapper 48 are omitted from the second manifold 42'. Without these components, however, some other means must be provided to vent excess oxygen from the apparatus to avoid destructive rupture of the oxygen reservoir bag 50'. In apparatus 110, the means for venting excess oxygen from the bag 50' are provided in the bag 50' itself. The structural details of these means as well as that of bag 50' will be more fully appreciated by reference to FIGS. 7 and 8 and the description thereof hereinafter.

FIGS. 3 through 6 graphically reflect various modalities of the oxygen an air inlet valves of the presently known resuscitator apparatus 110 shown in FIG. 2.

Figure 3:
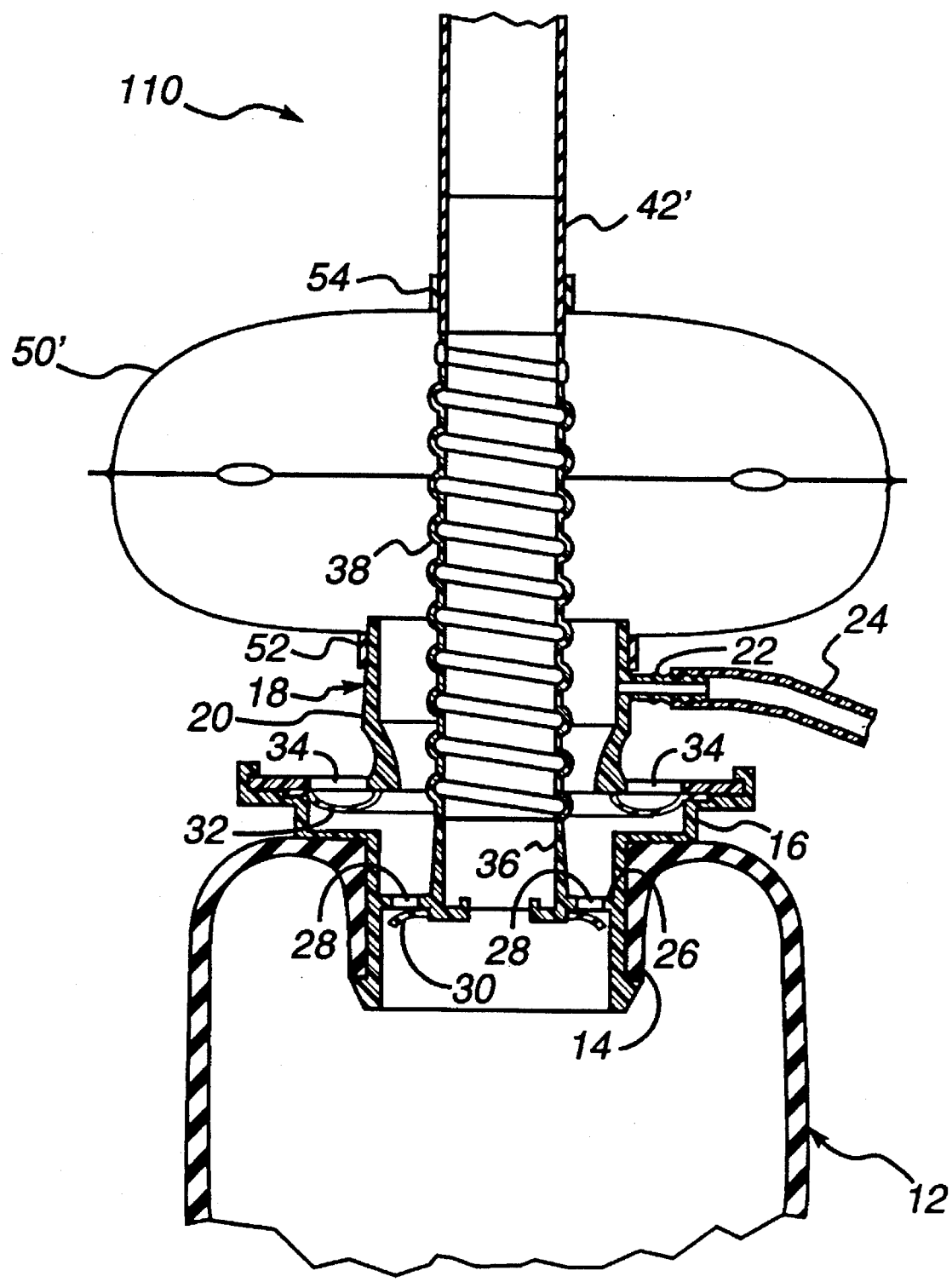
FIGS. 3, 4, 5 and 6 reveal various phases of operation of the squeeze bag resuscitator apparatus of FIG. 2.

Referring first to FIG. 3, the phase of resuscitation treatment depicted therein may be referred to as "unassisted oxygen administration." During this phase, the subject respires using his own efforts and the operator provides no external assistance such as periodic squeezing and releasing squeeze bag 12. Pressurized oxygen is continuously delivered via flexible conduit 24 through the oxygen inlet coupling and into the interior of the first manifold 18, hence inflating the oxygen reservoir bag 50' in fluid communication therewith.

When the subject inhales, a negative pressure is presented within the squeeze bag 12 thereby drawing the flapper valve 30, as illustrated, from sealing engagement with ports 28 through which the pressurized oxygen may flow to the subject. As inhalation ceases, flapper valve 30 closes ports 28, whereby oxygen that has been withdrawn from the oxygen reservoir bag 50' is replenished by new oxygen from the unillustrated oxygen supply. Upon exhalation, as is known, the non-rebreathing valve 64 (FIG. 2) vents the subject's expiratory gases to the atmosphere. Should the subject's rate of respiration be such that there exists prolonged intervals between inhalation, excess oxygen (designated herein by arrows 65 in FIG. 8), may be vented from the oxygen reservoir bag 50' through one or more slits 59 provided substantially at the equatorial region of the bag. The significance of the construction of bag 50', as well as the disadvantages arising therefrom, will be more fully appreciated from the discussion of FIGS. 7 and 8, infra.

Figure 4:
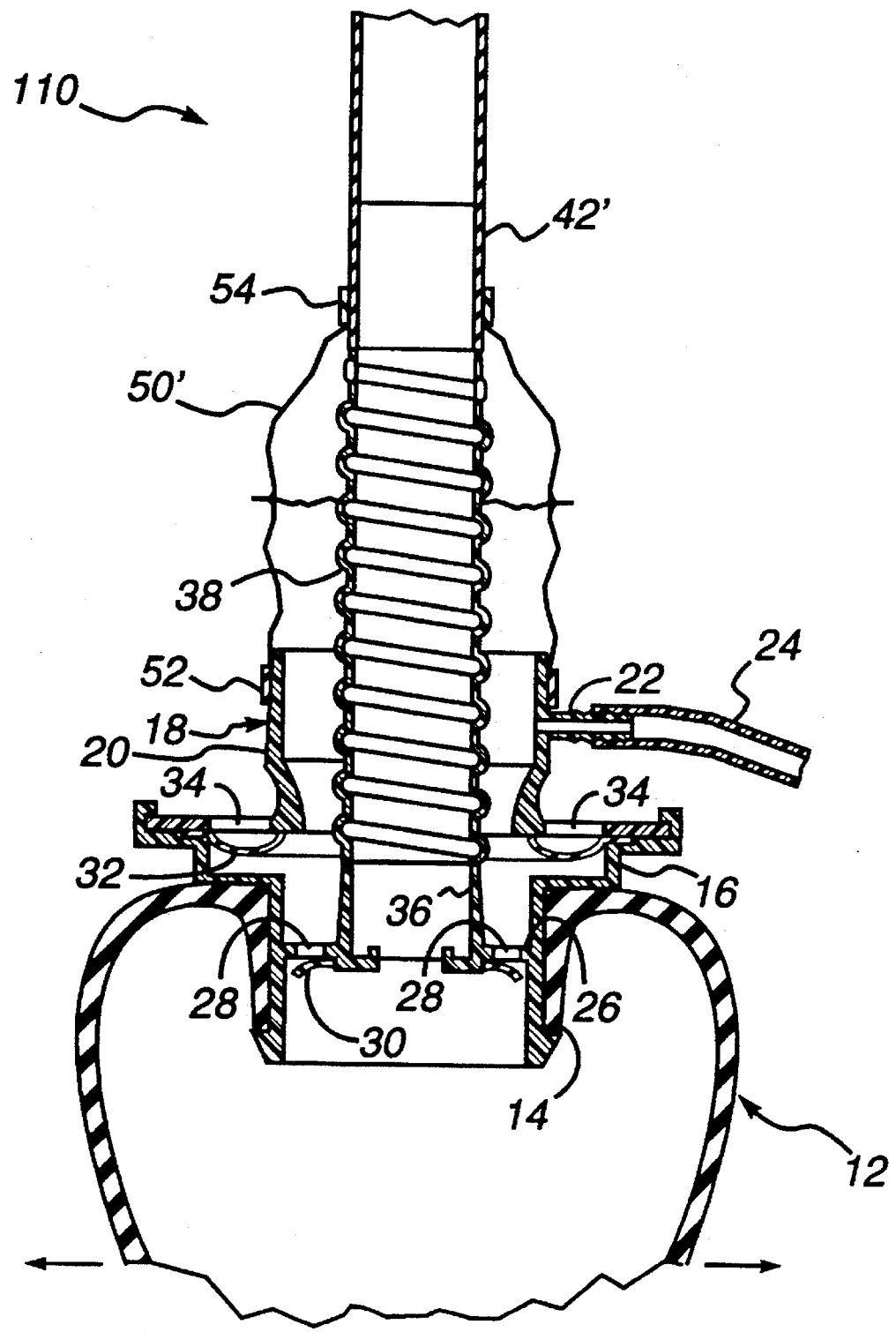

FIG. 4 represents a resuscitation treatment phase that may be categorized as "assisted oxygen administration: squeeze bag decompression." During this phase, the subject is typically exhaling and the operator is releasing squeezing pressure from the walls of the squeeze bag 12. As the squeeze bag is permitted to restore itself, negative pressure is created within the squeeze bag which pulls open the flapper valve 30 and draws oxygen into the squeeze bag from the oxygen reservoir bag 50' thereby deflating the latter.

Figure 5:
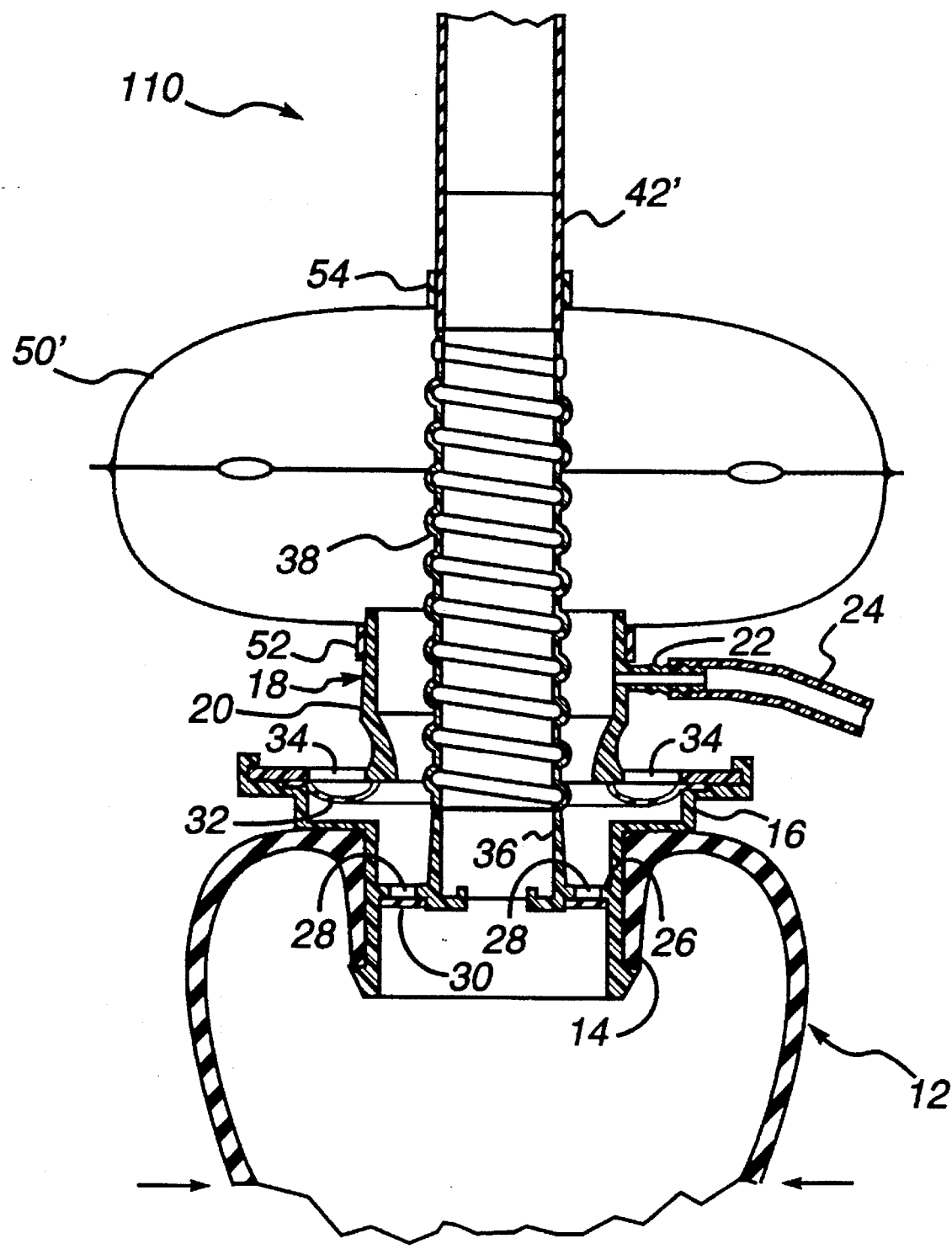

Once the squeeze bag is refilled with oxygen to the operator's satisfaction (which may entail a partial or total release of squeezing force from the walls of the squeeze bag), the resuscitation treatment enters its next phase, i.e., "assisted oxygen administration: squeeze bag compression," exemplified by FIG. 5. At this time the operator squeezes the squeeze bag, hence expelling the contents of the squeeze bag through the flexible hose 38, the non-rebreathing valve 64 and the mask 70 (FIG. 2) and into the subject's airway.

Figure 6:
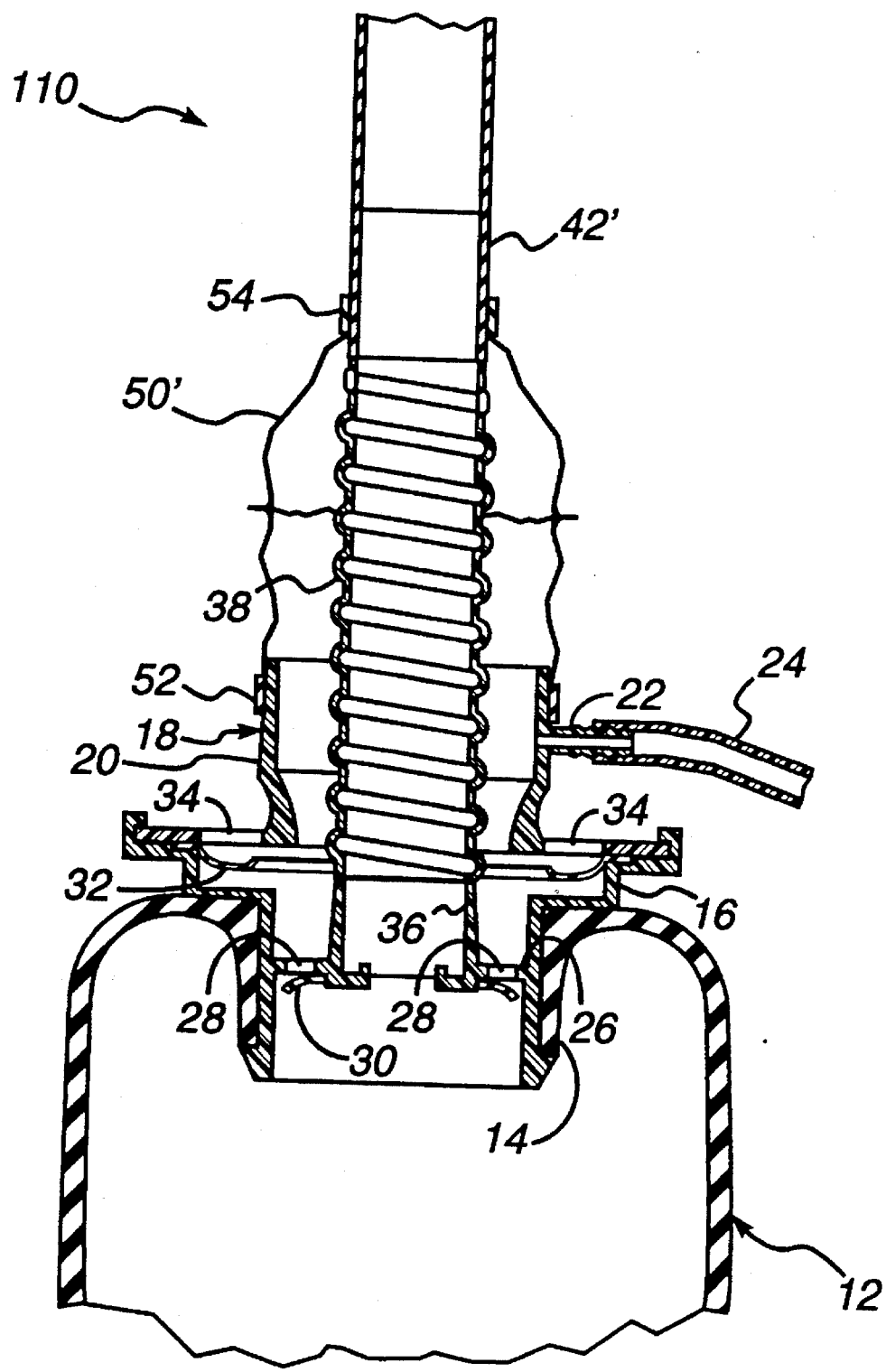

FIG. 6 represents a situation, identified herein as "unassisted ambient air administration" wherein oxygen is no longer being supplied to the resuscitator apparatus 110, either intentionally or unintentionally (e.g., the oxygen supply source becomes depleted or is temporarily interrupted for some other reason). Under these circumstances, in the absence of pressurized oxygen, the subject must inhale ambient atmospheric air. To do so, he must overcome not only the inherent spring bias of the flapper valve 30 but also the semi-toroidal flapper valve 32 (as shown) which normally closes the ambient air inlet ports 34 provided in the first manifold. The semi-toroidal cross-sectional configuration of the flapper valve 32 is deliberately formed therein so as to render the valve sufficiently stiff to resist ingress of atmospheric air through ports 34 under normal oxygen administration conditions, which air would mix with and thereby dilute the desired oxygen concentration.

Figure 7:
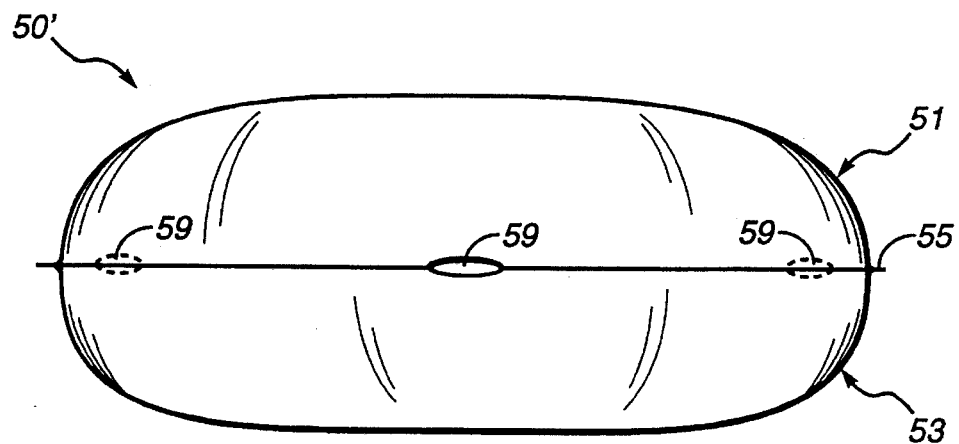
FIG. 7 is an enlarged elevational view of the oxygen reservoir bag of the squeeze bag resuscitator apparatus of FIG. 2, the oxygen reservoir bag being shown in inflated condition.
Figure 8:
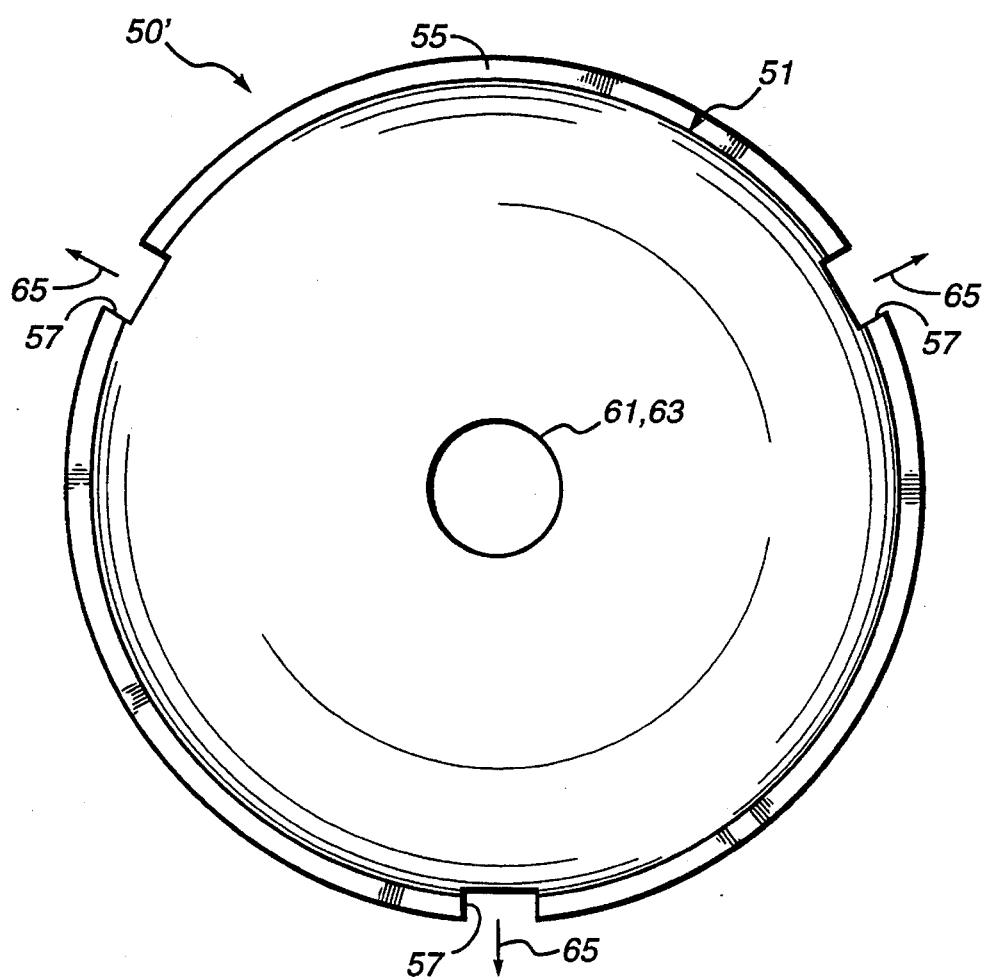
FIG. 8 is a plan view of the oxygen reservoir bag of FIG. 7.

FIGS. 7 and 8 depict on an enlarged scale the oxygen reservoir bag 50' of squeeze bag resuscitator apparatus 110. Bag 50' may be substantially spherical but more typically is oblate spheroidal in shape and is fabricated from thin (e.g., about 1.0 to 5.0 mil thick) pliable, non-self-restoring, non-porous, plastic material such as, for example polyurethane or polyethylene, although other plastics possessing similar physical characteristic would be equally acceptable. The bag 50' comprises two opposed, substantially hemispherical portions 51 and 53 which may be heat sealed, adhesively bonded or otherwise continuously affixed to one another to define a radially outwardly projecting equatorial flange or band 55. At least one notch 57 is cut from the band of a depth sufficient to form at least one generally horizontally extending slit 59 in the wall of the bag 50' substantially at the equator thereof. The opposite ends or poles 61,63 of the bag are open to permit their sealing attachment to the first and second manifolds 18 and 42' by adhesive tape 52 and 54 or other suitable fastening means.

As previously mentioned, when oxygen reservoir bag 50' is fully inflated, excess oxygen is vented from the slit(s) 59 as indicated by arrows 65 (FIG. 8). Experience has shown that cutting notches 57 from the equatorial band 55 to create slits 59 may reduce the bag's capacity to deliver essentially pure oxygen, particularly at low incoming oxygen flow rates. More specifically, at low incoming oxygen flow, e.g., 5 to 10 liters per minute, it has been discovered that, depending upon the vent geometry, ambient air may enter the bag through slits 59 or perhaps through the ambient air inlet ports 34 of the first manifold 18. Once inside, the air mixes with the oxygen thereby diluting its concentration. For the patient whose condition requires low-flow, highly purified oxygen resuscitation therapy, therefore, the efficacy of treatment using a resuscitator having an oxygen reservoir bag constructed like bag 50' may be less than desirable, if not entirely unacceptable. Vent geometry has also been shown to be a factor in detrimentally increasing AutoPEEP in prior resuscitator apparatus. As an example, certain vent geometry has demonstrated the capacity to vent excessive oxygen at elevated flow rates and afford a highly purified concentration of oxygen ultimately delivered to the patient. However, at high incoming oxygen flow, e.g., generally greater than about 50 liters per minute, presently known slitted oxygen reservoir bags such as bag 50' have contributed to excess pressurization of the resuscitator and, consequently, an undesirable level of AutoPEEP.

Figure 9:
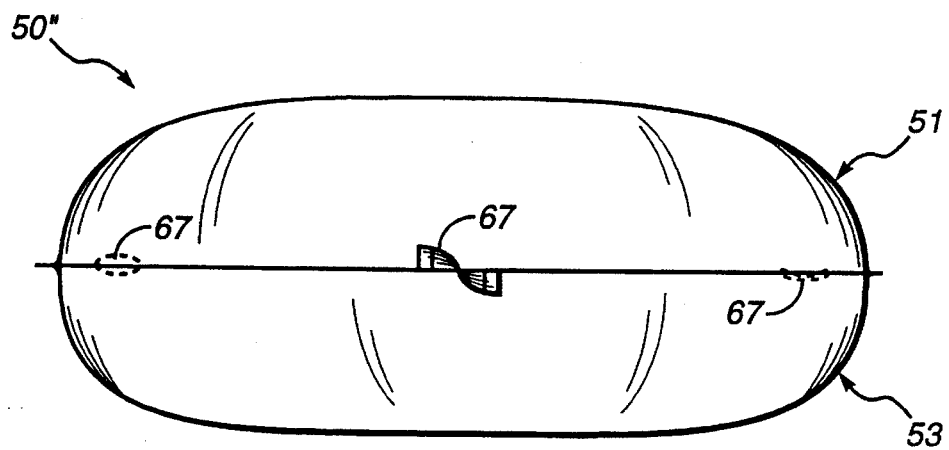
FIG. 9 is an enlarged elevational view of another conventional oxygen reservoir bag for a squeeze bag resuscitator apparatus, the oxygen reservoir bag being shown in inflated condition.
Figure 10:
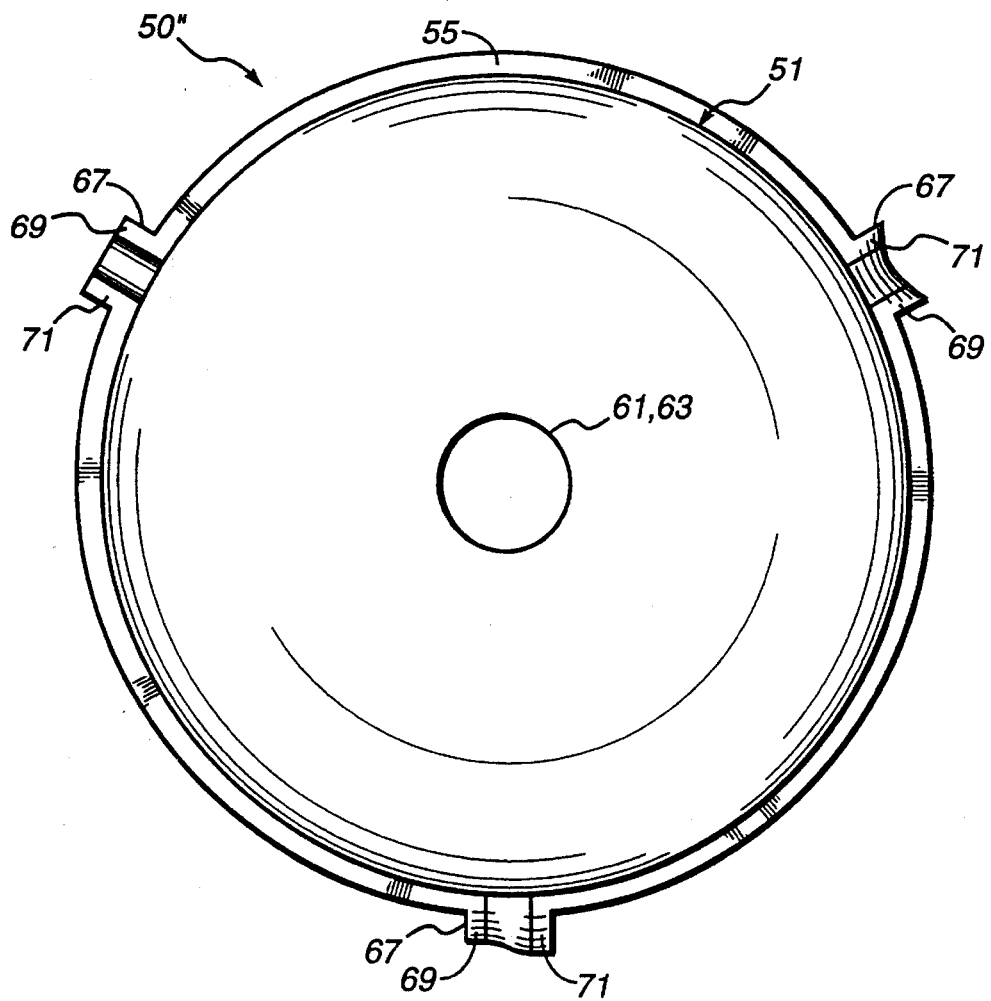
FIG. 10 is a plan view of the oxygen reservoir bag shown in FIG. 9.

Referring to FIGS. 9 and 10, there is shown an alternative design of oxygen reservoir bag, identified herein by reference numeral 50," that has been proposed for overcoming the structural deficiencies of bag 50' described above. In terms of its compositional material, configuration, mode of manufacture, installation and operation, bag 50" is substantially similar to bag 50' Accordingly, like reference numerals indicate elements similar to those earlier described, as is true in the remaining views. Thus, only those aspects of bag 50"

(and later described embodiments of the oxygen reservoir bag of the present invention) which depart materially in structure and/or function from their corresponding features of bag 50' will be addressed in detail.

The essential distinction between bag 50" and bag 50' lies in the construction of its excess oxygen pressure venting means, herein identified by reference numeral 67. Venting means 67 includes at least one flap-type conduit vent which projects radially outwardly from the bag 50" at at least one site along the equatorial band 55. Each flap is formed by providing a radially projecting tab on hemispherical portion 51 and a similar tab on hemispherical portion 53, and then aligning the tabs before continuously bonding the hemispherical portions along equatorial band 55. The opposed tab side edges 69 and 71 contiguous with the band 55 are similarly bonded such that the flap vent forms a conduit fluidly communicating the interior of the oxygen reservoir bag 50" with the ambient atmosphere.

Bag 50" also possesses an inherent design deficiency. Specifically, the area of the inlet to each vent 67 is substantially the same as that of the outlet thereof, i.e., the area of the vent opening at the juncture of the vent 67 with the bag 50" is essentially equal to that at the distal or free end of the vent from which oxygen is discharged into the atmosphere. Thus, the configuration of the vent itself prevents the vent from developing a suitable back pressure to reliably inflate the vent to maintain the shape of the vent's flow passageway when the bag 50" is inflated. The flap vents 67 thus tend to randomly twist, fold over and occlude under working pressure. Consequently, as illustrated, one or more of the vents frequently exhaust little or no oxygen from the bag. Excess oxygen pressure may therefore not be vented from the bag at a reliable and predicable rate such that internal resuscitator pressure and, concomitantly, AutoPEEP increases. Thickening of the bag including the vent regions thereof has been suggested as a remedy to this problem. However, increasing bag thickness operates to rigidify the bag and dampen its responsiveness to pressure fluctuations, as well as increase the cost to manufacture the resuscitator apparatus.

Figure 11:
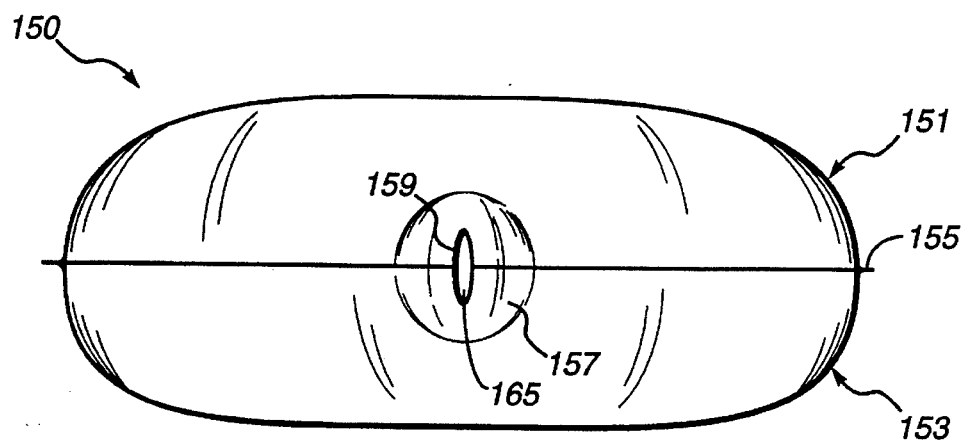
FIG. 11 is an enlarged elevational view of a first preferred embodiment of an oxygen reservoir bag constructed in accordance with the present invention, the oxygen reservoir bag being shown in inflated condition.
Figure 12:
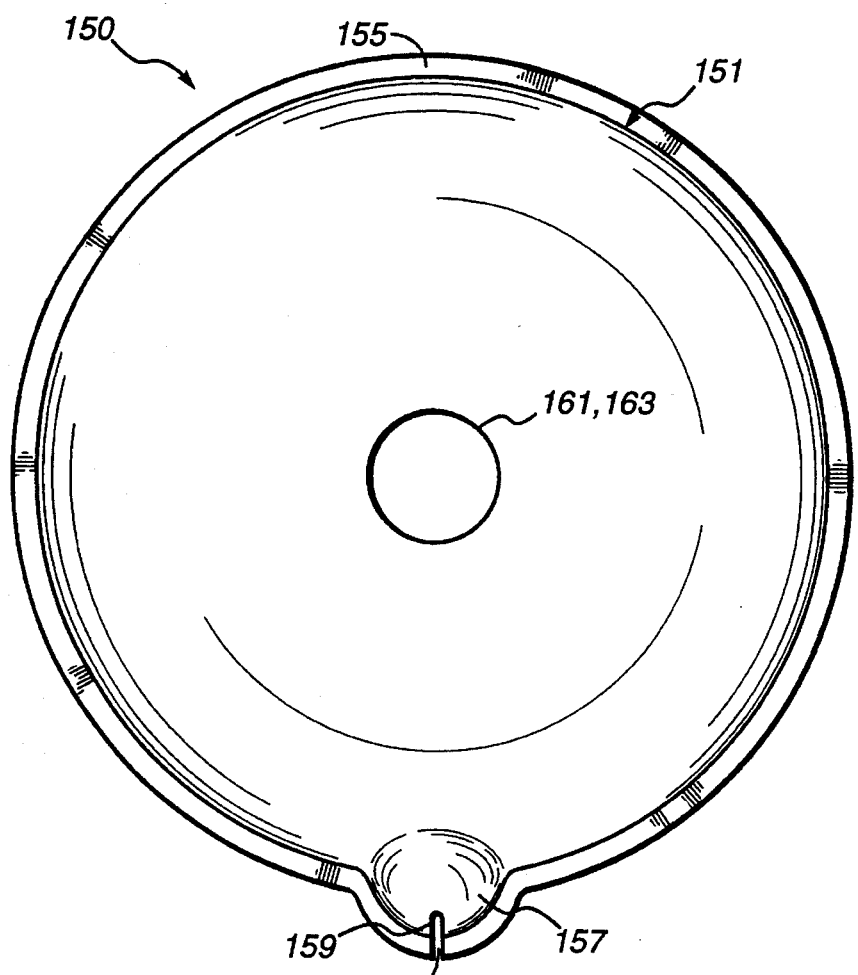
FIG. 12 is a plan view of the oxygen reservoir bag shown in FIG. 11.

Seeking an oxygen reservoir bag that would be inexpensive to manufacture, rugged, highly responsive to pressure fluctuations and capable of venting excess oxygen at predictable and reliable exhaust flow rates, enhancing oxygen concentration under low incoming oxygen flow and limiting AutoPEEP at elevated incoming oxygen flow, the present inventor has developed the novel oxygen reservoir bag of the instant invention, a first preferred embodiment of which is depicted in FIGS. 11 and 12 and identified by reference numeral 150.

Oxygen reservoir bag 150 may be (and preferably is) fabricated from the same materials an assembled in substantially the same way as bags 50' and 50" described hereinabove. That is, bag 150 may be generally spherical or, preferably, substantially oblate in shape. It is preferably manufactured from thin (e.g., about 1.0 to 5.0 mil thick), pliable, non-porous, non-self-restoring plastic material such as, for example, polyurethane or polyethylene, although other plastics possessing similar physical characteristics would be equally acceptable. Bag 150 further preferably comprises two opposed, substantially hemispherical portions 151 and 153 which may be heat sealed, adhesively bonded or otherwise continuously affixed to one another to define a radially outwardly projecting equatorial flange or band 155. Each of the hemispherical portions is provided with at least one protuberance, preferably of arced shape, which is aligned with a corresponding protuberance on the opposed hemispherical portion prior to affixation of the hemispherical portions to one another. Upon affixation of the hemispherical portions, these mating protruberances, establish at least one pocket 157 which forms a juncture with and extends radially outwardly from the equatorial region of oxygen reservoir bag 150. Each pocket 157 is in turn provided with vent means 159. Although the vent means may assume any orifice arrangement suitable to vent gas from bag 150, a presently preferred embodiment is that of a notch that traverses the equatorial band and at least one or, more desirably, both layers of plastic material which from the pocket. Having one pocket, the bag 150 represents an oxygen reservoir bag which is particularly well suited for a squeeze bag resuscitator apparatus designed for resuscitation of children. The "adult" version of such a bag is later described in connection with FIGS. 13 and 14.

Figure 15:
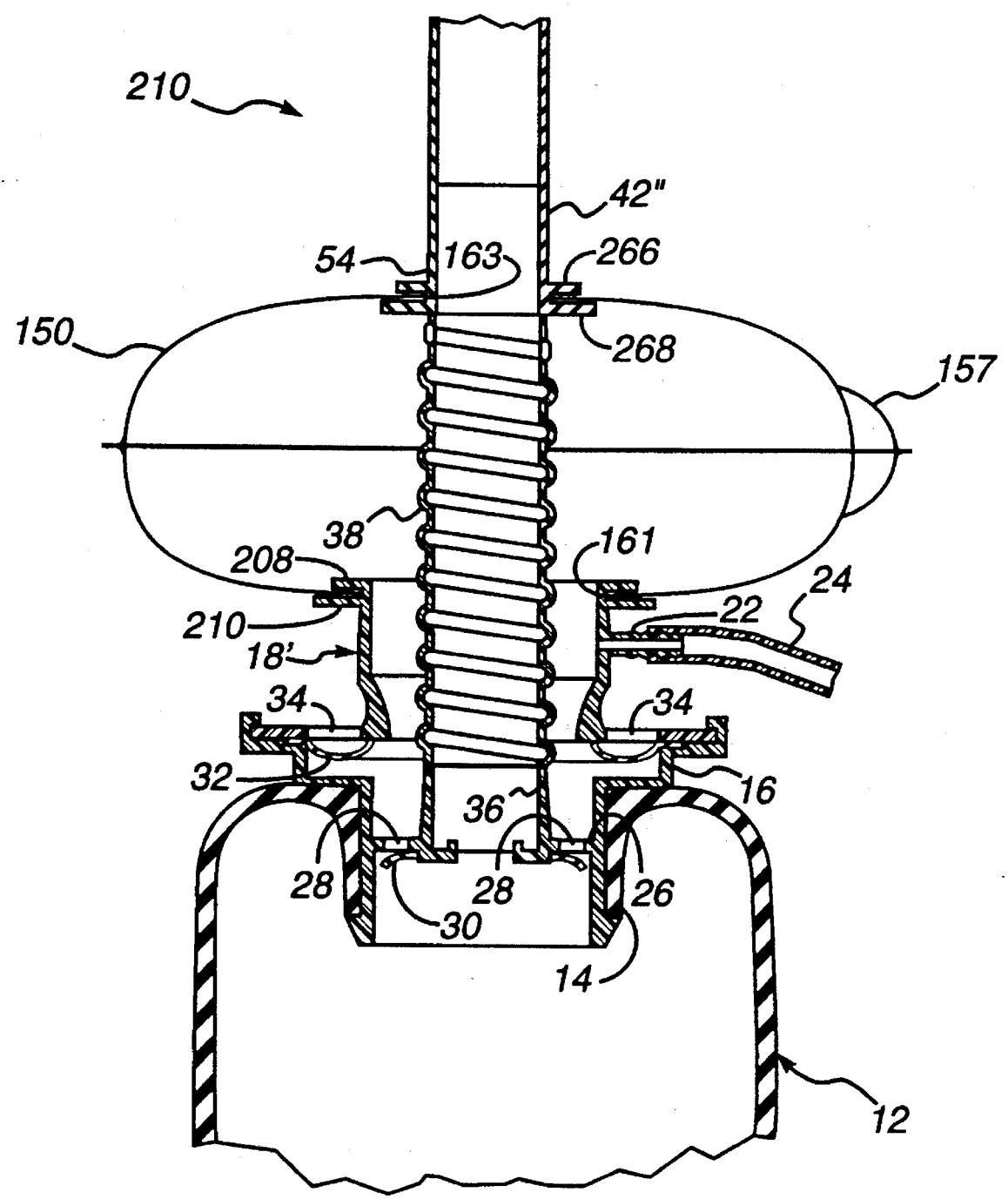
FIG. 15 is an elevational cross-section view of a squeeze bag resuscitator apparatus constructed according to the present invention, with the oxygen reservoir bag of FIGS. 11 and 12 installed thereon.

And, similar to oxygen reservoir bags 50, 50' and 50", bag 150 (as well as later-described bag 150') includes polar openings, identified herein by reference numerals 161,163 for permitting attachment of the bag to first and second manifolds (FIG. 15).

Upon inflation of the bag 150 with oxygen, as shown in FIGS. 11 and 12, the pocket 157 likewise inflates to form a bulbous formation which bulges from the equatorial region of the bag. Concurrently, the vent means 159 opens up to form an aperture 165 that extends substantially normal to and, preferably, spans the bag's equator.

Unlike the flap type vents 67 of the bag 50" discussed supra, the flow passageway of the pocket 157 is non-uniform in cross-section throughout its length. More particularly, the area of the inlet opening to each pocket at the juncture of the pocket and the equatorial region of the bag is greater than that of the outlet opening of the pocket, i.e., the area of the pocket opening at the juncture of the pocket with the bag 150 is substantially greater than the area of aperture 165 at the distal end of the pocket from which excess oxygen is vented. So constructed, the pocket 157 develops an internal back pressure operable to reliably inflate the pocket, much like a sail or parachute, upon inflation of bag 150. As a result, unintended twisting, folding or other occlusion of the pocket is effectively prevented. In addition, the pressurized pocket inhibits ingress of atmospheric air through aperture 165 and other ambient air interface sites, even at very low incoming oxygen flow rates. And, once inflated, the contours of the bulbous formation created by the pocket serve to funnel oxygen flow toward the aperture 165 and function as oxygen collection sites to maintain high oxygen concentration within the bag 150 under low incoming flow rates.

Moreover, bag 150 and bag 150' (discussed infra) perform favorably at all incoming oxygen flow rates typically encountered in oxygen-enhanced resuscitation treatment. Hence, a resuscitator apparatus equipped with either bag 150 or 150' delivers highly concentrated oxygen at incoming oxygen flow rates ranging from as low as about 5 to 10 liters per minute to as high as about 80 liters per minute. Indeed, even at 80 liters per minute incoming oxygen flow, the unique construction of the oxygen reservoir bags of the present invention limit AutoPEEP to less than about 3cmH$_2$O. Currently available resuscitators, by contrast, achieve comparable AutoPEEP control at incoming oxygen flow rates of generally no greater than about 30 liters per minute.

Figure 13:
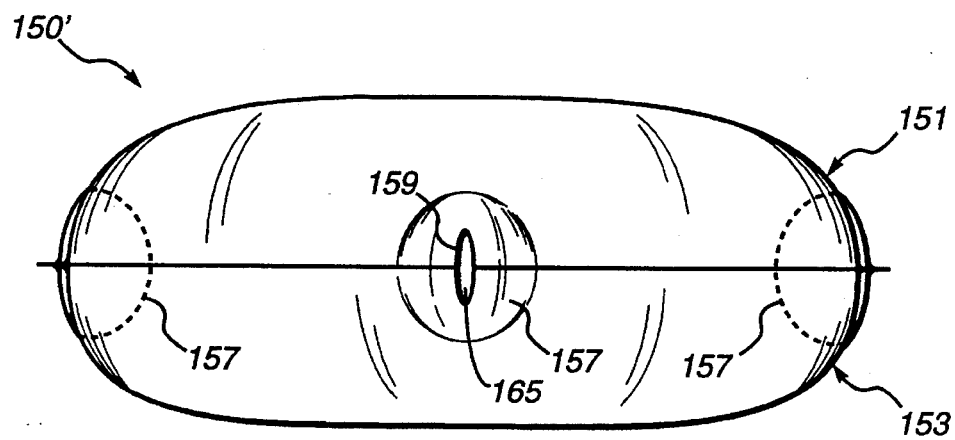
FIG. 13 is an enlarged elevational view of a further preferred embodiment of an oxygen reservoir bag constructed according to the present invention, the oxygen reservoir bag being shown in inflated condition.
Figure 14:
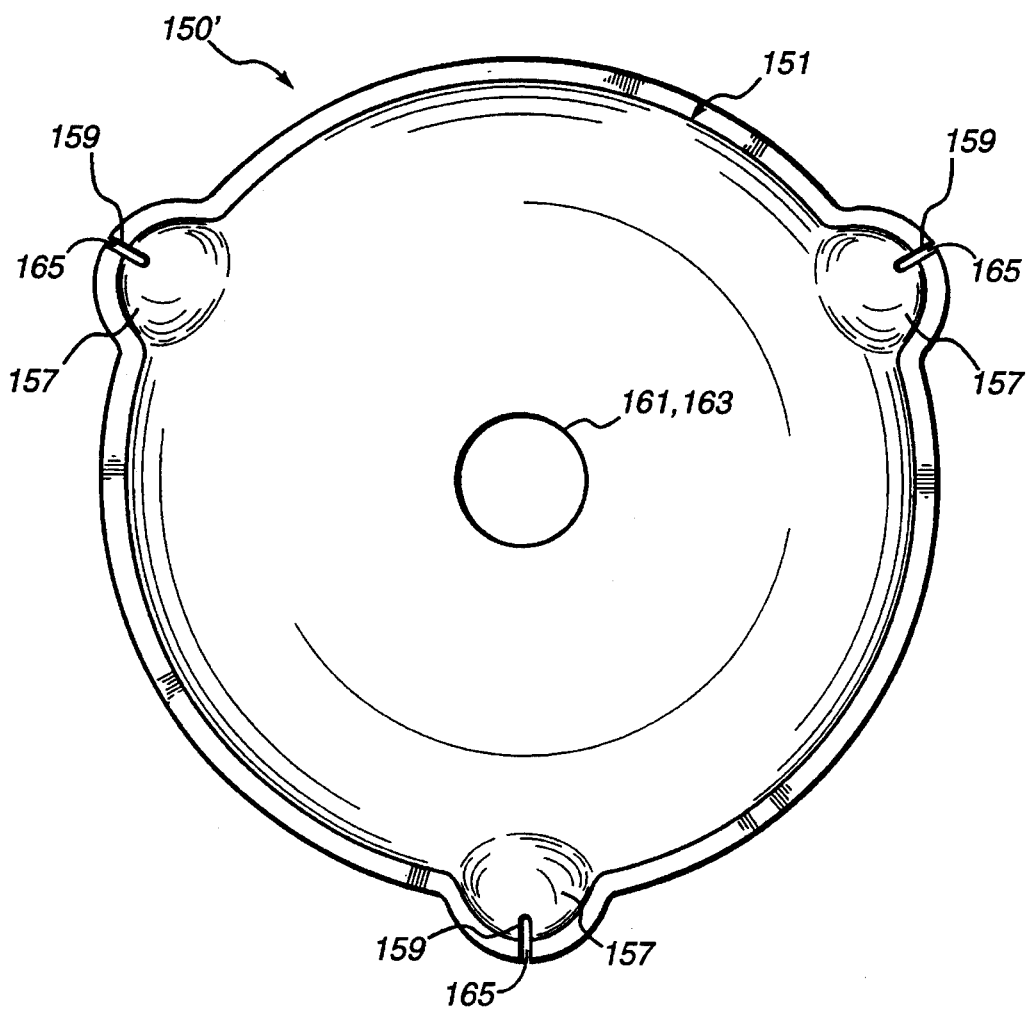
FIG. 14 is a plan view of the oxygen reservoir bag shown in FIG. 13.

Referring to FIGS. 13 and 14, there is shown a further preferred embodiment of an oxygen reservoir bag constructed according to the present invention and identified herein by reference numeral 150'. Bag 150' is particularly well suited to accommodate the higher incoming oxygen flow rates normally required by the adult patient population. Apart from having a plurality of pockets 157 (and attendant apertures 165) preferably equiangularly spaced about its equatorial region, bag 150' is substantially identical in structure and function to bag 150. Further, although three pockets are shown, bag 150' may have two, four or even more pockets so long as oxygen exhaust capability and bag integrity are not compromised.

In the aggregate, therefore, oxygen reservoir bags 150 and 150' represent economical, durable and reliable alternatives to existing oxygen reservoir bags for squeeze bag resuscitators. Additionally, bags 150 and 150' may be readily manufactured using existing materials and, with minor modifications, conventional techniques.

FIG. 15 exhibits most clearly a further aspect of the present invention, namely, a novel squeeze bag resuscitator apparatus 210 fitted with oxygen reservoir bag 150. It will be understood that apparatus 210 may just as easily be fitted with bag 150' since, as previously mentioned, but for having a plurality of pockets 157, the essential components and construction of bag 150' are generally identical to bag 150. Further, apparatus 210, except where otherwise indicated, is constructed and functions substantially similarly to apparatus 110 of FIGS. 2 through 6. Hence, those elements of apparatus 210 bearing the same reference numerals as elements of apparatus 110 may be considered substantially identical in structure and function to their counterparts in FIGS. 2 through 6. Accordingly, only those components of FIG. 15 which depart materially in structure and/or function from those described in connection with FIGS. 2 through 6, or whose description is otherwise required for a proper understanding of the invention, will be discussed in detail.

A first manifold 18' of squeeze bag apparatus 210 is preferably formed with spaced apart, radially outwardly projecting upper and lower flanges 208 and 210. Likewise, a second manifold 42" is constructed with similar flanges 266 and 268. The lower polar opening 161 of the oxygen reservoir bag 150 is sized such that it must be stretched over flange 208 of the first manifold 18'. Once the flange 208 has been cleared, the bag opening may be released whereby it contracts within the groove formed between flanges 208 and 210 and comes into tight gripping and pneumatic sealing engagement with the first manifold 18' The opposite polar opening 163 of the oxygen reservoir bag 150 is similarly secured in the groove formed between flanges 266 and 268 of the second manifold 42". As the exterior surfaces of the first and second manifolds in the grooves between flanges 208, 210 and 266, 268 are generally from about 1.5 to 1.7 inches in diameter, the openings at the opposite ends of the oxygen reservoir bag 150 are preferably pre-cut to approximately 0.5 inch in diameter to assure that they snap into contact with the manifold housings. Although the foregoing example is merely for purpose of illustration, it will be understood that polar openings 161 and 163 shall be pre-cut to any dimensions as may be needed to sealingly engage with first and second manifolds of any size and shape. Thus, the oxygen reservoir bag 150 is capable of sealing attachment to the resuscitator apparatus 210 without resort to adhesive tape or other supplemental fastening means.

Moreover, if desired, bags 150 and 150' may be installed with tape, adhesives or other suitable attachment means onto squeeze bag apparatus having conventional, i.e., non-flanged, first and second manifolds.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A bag formed of pliable, non-porous material, said bag being operable to store pressurized gas and fluidly and sealingly connect first and second members, said bag comprising:

a substantially spherical body including first and second substantially hemispherical portions and an equatorial region defining an equator;

a first opening at a polar region of said first hemispherical portion for receiving said first member;

a second opening at a polar region of said second hemispherical portion for receiving said second member;

at least one radially outwardly projecting pocket forming a juncture with said equatorial region; and vent means provided in said at least one pocket for venting excess quantities of said pressurized gas from said bag to the atmosphere, whereby upon inflation of said bag with said pressurized gas, said at least one pocket forms at least one bulbous formation bulging radially outwardly from said equatorial region and said vent means vents said excess quantities of said pressurized gas from said bag to the atmosphere.

2. The bag of claim 1 wherein said juncture of said at least one pocket with said equatorial region defines a pocket inlet opening, said pocket inlet opening being larger in area than said vent means.

3. The bag of claim 1 wherein said vent means comprises an aperture extending substantially normal to said equator.

4. The bag of claim 3 wherein said aperture spans said equator.

5. The bag of claim 1 wherein said at least one pocket comprises a plurality of pockets forming a plurality of junctures with said equatorial region.

6. The bag of claim 5 wherein said vent means is provided in each of said plurality of pockets.

7. An assembly for use in a resuscitator apparatus equipped with a squeeze bag, said squeeze bag having an opening and formed of compressible material, said assembly comprising:

a first manifold having a groove and means for connecting said first manifold to said squeeze bag;

a second manifold having a groove; and a pliable bag adapted to store pressurized breathing gas supplied to said first manifold, said bag having an equatorial region and openings at first and second polar regions thereof, a first of said openings self-sealingly engaging said first manifold groove and a second of said openings self-sealingly engaging said second manifold groove, said pliable bag further including:

at least one radially outwardly projecting pocket forming a juncture with said equatorial region; and vent means provided in said at least one pocket for venting excess quantities of said pressurized gas from said bag to the atmosphere, whereby upon inflation of said bag with said pressurized gas, said at least one pocket forms at least one bulbous formation bulging radially outwardly from said equatorial region and said vent means vents said excess quantities of said pressurized gas from said bag to the atmosphere.

8. The assembly of claim 7 wherein said first and second openings of said bag are of smaller size than, respectively, said first manifold groove and said second manifold groove.

9. The assembly of claim 8 wherein said first manifold comprises a pair of spaced-apart radially outwardly directed flanges, said first manifold groove being disposed between said flanges.

10. The assembly of claim 7 wherein said second manifold comprises a pair of spaced apart radially outwardly directed flanges, said second manifold groove being disposed between said flanges.

11. The assembly of claim 7 wherein said juncture of said at least one pocket with said equatorial region defines a pocket inlet opening, said pocket inlet opening being larger in area than said vent means.

12. The assembly of claim 7 wherein said vent means comprises an aperture extending substantially normal to said equator.

13. The assembly of claim 12 wherein said aperture spans said equator.

14. The assembly of claim 7 wherein said at least one pocket comprises a plurality of pockets forming a plurality of junctures with said equatorial region.

15. The assembly of claim 14 wherein said vent means is provided in each of said plurality of pockets.

\* \* \* \* \*